(12) United States Patent
Eibl

(10) Patent No.: US 7,795,399 B2
(45) Date of Patent: Sep. 14, 2010

(54) STABLE THERAPEUTIC PROTEINS

(75) Inventor: Johann Eibl, Vienna (AT)

(73) Assignee: Bio & Bio Licensing SA, Luxembourg (LU)

( * ) Notice: Subject to any disclaimer, the term of this patent is extended or adjusted under 35 U.S.C. 154(b) by 0 days.

(21) Appl. No.: 11/155,416

(22) Filed: Jun. 17, 2005

(65) Prior Publication Data

US 2006/0009376 A1 Jan. 12, 2006

Related U.S. Application Data

(63) Continuation of application No. PCT/AT03/00374, filed on Dec. 18, 2003.

(30) Foreign Application Priority Data

Dec. 18, 2002 (AT) ............... A 1890/2002

(51) Int. Cl.
*A61K 38/48* (2006.01)
*G01N 33/53* (2006.01)
(52) U.S. Cl. .............. 530/384; 435/7.71; 930/250
(58) Field of Classification Search .............. None
See application file for complete search history.

(56) References Cited

U.S. PATENT DOCUMENTS

| 4,297,344 | A | * | 10/1981 | Schwinn et al. ............. 530/381 |
| 4,348,384 | A | * | 9/1982 | Horikoshi et al. ........... 424/450 |
| 4,440,679 | A | * | 4/1984 | Fernandes et al. ........... 530/363 |
| 4,710,381 | A | | 12/1987 | Kunicki et al. |
| 4,814,435 | A | | 3/1989 | Schwarz et al. |
| 5,149,787 | A | | 9/1992 | Kunicki et al. |
| 5,175,087 | A | * | 12/1992 | Ranby et al. ................. 435/13 |
| 5,278,289 | A | | 1/1994 | Johnson et al. |
| 5,457,181 | A | | 10/1995 | Michalski et al. |
| 5,484,890 | A | | 1/1996 | Johnson et al. |
| 5,614,500 | A | | 3/1997 | Zimmermann |
| 5,645,540 | A | * | 7/1997 | Henniges et al. ............. 604/320 |
| 5,804,400 | A | | 9/1998 | Martin et al. |
| 5,874,407 | A | * | 2/1999 | Kelley et al. ................. 514/12 |
| 2001/0033837 | A1 | * | 10/2001 | Metzner et al. ............. 424/94.3 |

FOREIGN PATENT DOCUMENTS

| EP | 0270291 | 6/1988 |
| EP | 1161958 | 12/2001 |
| JP | 9286797 | 11/1997 |
| WO | WO 9305067 | 3/1993 |

OTHER PUBLICATIONS

Tolo, et al., Journal of Interferon and Cytokine Research, 21, 913-920.*
[Retrieved from] 'http://en.wikipedia.org/wiki/Protease', 3 pages, Jan. 26, 2007.*
[Retreived from] http://www.thefreedictionary.com/allogenic, 2009, 3 pages [Retreived on Sep. 2, 2009].*
Nissen, 1998, International Immunology, 10, 167-173.*
Hemker HC. Thrombin Generation in a Reconstituted System: A Comment. Thromb Haemost 2002; 87:551-552.
Mann et al., Thrombin Generation in a Reconstituted System: A Reply. Thromb Haemost 2002; 87:552-554.
Mutch et al., Human Thrombi Contain an Abundance of Active Thrombin. Thromb Haemost 2001; 86:1028-1034.
Siebenlist et al., Protansglutaminase (Factor XIII) Mediated Crosslinking of Fibrinogen and Fibrin. Thromb Haemost 2001; 86:1221-1228.
Brummel et al., An Integrated Study of Fibrinogen during Blood Coagulation. J Biol Chem 1999; 274:22862-22870.
Fischer et al., Immobilized hirudin and hirudin-based peptides used for the purification of recombinant human thrombin prepared from recombinant human prothrombin. Protein Expr Purif. 1996 8(2):167-174.
Feldman et al., Large-scale preparation and biochemical characterization of a new high purity factor IX concentrate prepared by metal chelate affinity chromatography. Blood Coagul Fibrinolysis. 1994, 5(6):939-948.
Lawson et al.,. A Model for the Tissue Factor Pathway to Thrombin. J Biol Chem 1994; 269:23357-23366.
Kulseth et al., A highly sensitive chromogenic microplate assay for quantification of rat and human plasminogen. Anal Biochem. 1993, 210,(2): 314-317.
Andersson et al., Isolation and characterization of human factor VIII: Molecular forms in commercial factor VIII concentrate, cryoprecipitate, and plasma. Proc Natl Acad Sci 1986; 83:2979-2983.
Eaton et al. Proteolytic Processing of Human Factor VIII. Correlation of Specific Cleavages by Thrombin, Factor Xa, and Activated Protein C with Activation and Inactivation of Factor VIII Coagulant Activity. Biochemistry 1986; 25:505-512.
Rotblat et al., Purification of Human Factor VIII:C and Its Characterization by Western Blotting Using Monoclonal Antibodies. Biochemistry 1985; 24:4294-4300.
Monsigny et al., Assay for proteolytic activity using a new fluorogenic substrate (peptidyl-3-amino-9-ethyl-carbazole); quantitative determination of lipopolysaccharide at the level of one picogram. EMBO J. 1982;1(3):303-306.

* cited by examiner

*Primary Examiner*—Andrew D Kosar
*Assistant Examiner*—Satyanarayana R Gudibande
(74) *Attorney, Agent, or Firm*—Baker Botts LLP

(57) ABSTRACT

The invention relates to storable medicaments produced from pharmaceutical active ingredient preparations which are virus safe. Said medicaments contain at least one intact therapeutic protein obtained from plasma or by means of genetic engineering, as an active pharmaceutical substance. Said active ingredient preparations contain active enzymes, especially proteases, which are either free or bound to the substrates thereof and act against the therapeutic protein(s) present.

11 Claims, No Drawings

STABLE THERAPEUTIC PROTEINS

CROSS REFERENCE TO RELATED APPLICATIONS

This application is a continuation of International Patent Application No. PCT/AT2003/000374 filed Dec. 18, 2003, designating the United States and published in German on Jul. 1, 2004 under International Patent Publication No. WO 2004/054607, which is based on Austrian Patent Application No. A 1890/2002 filed Dec. 18, 2002, to each of which priority is claimed, and each of which is incorporated by reference in its entirety herein.

FEDERALLY FUNDED GRANT SUPPORT

Not applicable.

1. INTRODUCTION

The present invention relates to methods for maintaining the integrity and stability of therapeutic proteins during recovery, purification and storage.

2. BACKGROUND OF THE INVENTION

Therapeutic proteins have been used in the medical field for more than 100 years and are constantly gaining in medical interest and significance. Comparisons with other active pharmaceutical substances show that therapeutic proteins as albuminous substances exhibit a significantly lower stability and a higher degree of impurities. In comparison with other pharmaceutical drug substances, therapeutic proteins also exhibit a relatively high sensitivity to various chemical and physical factors, in particular to enzymes auch as proteases that cleave peptide bonds. Therefore, all measures which, during the recovery, purification and storage of intact therapeutic proteins, contribute to maintaining their integrity and stability are of great economic importance.

Changes in therapeutic proteins—and that applies to all proteins—may be effected by intramolecular rearrangements or chemical reactions such as the cleavage or formation of covalent bonds. An enzyme which recognizes a therapeutic protein as its substrate is able to largely change the same and, as far as a protease is concerned, may result in one or more cleavages in the peptide chain of the protein. Such enzymes as well as their precursors, which are referred to as proenzymes or—as in the case of proteases—also as zymogens, can already be contained in the starting materials for the production of natural therapeutic proteins as well as those obtained by genetic engineering. Enzymes which act upon proteins are proteins themselves in most cases and can be provided both in the free state and as already bound to their substrates. Zymogens may also be provided as substrates or may already be bound to their specific enzymes which they convert to proteases.

Enzymatic effects on therapeutic proteins during their manufacture and storage, ranging from the starting product to the final product, may lead to high losses and instable final products (Anderson et al. 1986; Eaton et al. 1986; Brummel et al. 1999).

Enzymes acting upon therapeutic proteins as well as their proenzymes and procofactors, which, by activation, lead to the formation of further such enzymes during the purification procedure, are already present in many starting materials. Procofactors also are proteins which are disintegrated into cofactors by the effect of proteases without being enzymes themselves. Cofactors specifically increase certain protease activities many times over.

Such enzymes, proenzymes, cofactors or procofactors may themselves be utilized as therapeutic proteins, provided that viral pathogens as they can be present in blood or in biomasses obtained by genetic engineering were inactivated or depleted, respectively, by inactivation or cleansing processes in the course of preparing the pharmaceutically active substance.

The blood clotting cascade is one of the best known enzyme systems. It is triggered by an enzyme cofactor, the lipid-containing tissue factor, which increases the enzyme activity of Clotting Factor VIIa many times over. The tissue factor normally is found only in cells and therefore cannot enter a relationship of interaction with Clotting Factor VIIa. Due to pathologic or traumatic events, the tissue factor may reach the surface of tissue factor-containing cells or may leave those cells, respectively. By means of the small amounts of Factor VIIa which always are present in the blood, the enzyme cascade may then be initiated. The final point of that clotting cascade is the enzyme thrombin which is formed in this way via the extrinsic and common pathway and transforms fibrinogen to fibrin. Fibrinogen, which may also be used as a therapeutic protein, is cleaved into fibrin monomer and fibrinopeptides by thrombin. Fibrin monomer polymerizes into fibrin strands and finally into a network which may bring about a closure of the wound in the wound bed and hence the termination of bleeding. Fibrinogen neither is an enzyme nor does it possess any cofactor properties (Lawson et al. 1994; Hemker 2002; Mann et al. 2002).

However, thrombin does not only have an enzymatic effect on fibrinogen but, among other things, it also converts the proenzyme of Clotting Factor XIII to the enzyme of Clotting Factor XIIIa. By means of cross linkages between the fibrin strands in the three-dimensional fibrin scaffold, said enzyme acting as transglutaminase gives rise to an increased biomechanical stability of the fibrin network that was formed as well as to a protection from enzymatic degradation. In the blood or plasma, respectively, which has clotted due to the effect of thrombin, further important enzymatic processes arise, in particular the formation of thrombin from the proenzyme prothrombin, the Clotting Factor II. That brings about a strong increase in the thrombin concentration in the clotted blood, which does not only cause the complete conversion of Clotting Factor XIII to that of XIIIa, but also the activation of proenzyme TAFI into enzyme TAFIa. Said enzyme cleaves off a short peptide from the fibrin, which short peptide contains receptors for a fibrinolytic enzyme complex and thus serves for the resistance of fibrin to any fibrinolytic effects. For those processes, a relatively high concentration of thrombin in the already clotted blood is necessary, which may be generated by activating the prothrombin present in the clotted blood (Siebenlist et al. 2001).

The strongly increased formation of thrombin in the blood clot itself is no longer accomplished via the extrinsic tenase pathway but via the intrinsic tenase and the common pathways. Small amounts of thrombin in the presence of Factor VIII and Factor IXa and of any clotting-promoting phospholipid already lead to the formation of the intrinsic tenase complex, which, just like the extrinsic tenase complex but 50 times stronger, causes the activation of Clotting Factor X in Xa by proteolytic cleavage, which then leads to the formation of thrombin by the activation of prothrombin (Mutch et al. 2001).

In physiological as well as in pathophysiological clotting processes, certain cellular phospholipid structures in and on cells, in particular in blood platelets, trigger a strong additional acceleration of certain enzymatic processes in the clotting cascade, in addition to the activity-increasing, high-molecular cofactors.

Already in the hitherto known methods for the recovery of therapeutic proteins, purification conditions were applied which endeavoured to minimize the enzymatic effects on the proteins to be obtained, for instance, by carrying out the purification process at temperatures as low as possible and/or by the addition of inhibitors (Kunicki et al. 1987 and 1992; Johnson et al. 1994 and 1996; Rotblat et al. 1985). Nevertheless said procedure did not turn out to be sufficient, in particular in case of proteins which are subject to easy enzymatic cleavage. The cleansing of such enzymes, its proenzymes, cofactors and procofactors also was not done sufficiently enough in quantitative terms during the purification process and hence the reproduction of such enzymes throughout the entire manufacturing process was not taken into sufficient account, either. For that reason, many of the hitherto obtained therapeutic proteins were characterized by merely an insufficient yield with changed and decreased biological efficiency as well as great instability, in particular during the necessary storage of the finished drug composition.

The enzyme inhibitors that have so far been used for purification exhibited an avidity and/or a concentration which were too low. Therefore, enzymes which were already bound to their substrates could be neutralized only insufficiently. Furthermore, it also was not taken into account to keep the concentration of enzyme inhibitors as constant as possible during the purification process.

It is possible that therapeutic proteins obtained by genetic engineering may already have bound proteolytic enzymes when being expressed and discharged from the cells, or they may bind those, respectively, which are present in the culture medium. The same also applies to therapeutic plasma proteins. During the recovery, storage and processing of plasma, especially proteolytic enzymes which recognize plasma proteins as their substrates can be formed. In doing so, at first protease-substrate complexes are formed and, in the following, the substrate is enzymatically cleaved.

After that kind of complex formation involving a therapeutic protein as a high-molecular substrate, proteases are no longer or only to a minor extent inhibitable by inhibitors. By those processes, therapeutic proteins may undergo a substantial change in quality or be largely destroyed already during their manufacture and especially their storage.

Already in the first fractionation process of the cryoprecipitation of plasma, enzyme-mediated changes in the cryoprecipitate and in the cryoprecipitate supernatant may occur, resulting in a poorer yield and a reduction in quality of the therapeutic proteins obtained at a later stage of the manufacturing process. This applies in particular to Clotting Factor VIII obtainable from cryoprecipitate. Enzymatic processes in the cryoprecipitate may also lead to the activation of Clotting Factor XIII, which, together with thrombin, is responsible for the increased formation of fibrin monomer complexes. Fibrin monomer complexes have an adverse effect on the quality of the fibrinogen obtainable from cryoprecipitate.

A mixture of clotting factors can be eluted from the supernatant of the cryoprecipitation by binding to weak anion exchangers and elution with saline solutions. Said mixture contains basically Clotting Factors II, VII, IX and X and is referred to as a prothrombin complex. It is also possible to isolate individual clotting factors from the prothrombin complex, processing them further into a pharmaceutical preparation. The prothrombin complex, processed further into a pharmaceutical preparation, must pass through further manufacturing steps in order to guarantee an extensive removal of possibly present viruses. These manufacturing steps must be carried out at room temperature or at an increased room temperature. Due to the starting material and the production, there is the possibility that clotting factors present in the prothrombin complex are activated, which, in the parenteral application of the prothrombin complex, are at least also involved in side effects of said product which may manifest themselves as peripheral occlusions, myocardial infarctions, pulmonary embolisms or strokes. Therefore, the object is to obtain the clotting factors contained in the prothrombin complex in such a way that they are activated neither during storage, nor during the manufacturing process, nor during the subsequent application.

Activations of zymogens play an adverse role also during the recovery of thrombin, plasminogen and immunoglobulins obtained from different fractions of the cryoprecipitation supernatant.

Thrombin can be contaminated, for instance, by plasmin evolving from its zymogen, plasminogen, and therefore might exhibit insufficient haemostatic activity. According to the plasmin content, the result is a premature loosening of the wound closure and a reoccurrence of bleeding.

Activations of zymogens also play an important role in the recovery of immunoglobulins. By plasmin, immunoglobulin G is cleaved, for example, into a Fab-fragment and a Fc-piece. If the immunoglobulin G is applied parenterally, this enzymatic cleavage of the immunoglobulin leads to a strongly reduced half-life and to a reduction in quality of the antibodies contained in the immunoglobulin preparation. For therapeutic purposes, it is often necessary to administer large amounts of immunoglobulin G—up to 250 g per patient. In this connection, severe side effects have repeatedly been reported, such as myocardial infarctions and central vascular occlusions. It therefore is of utmost importance to produce immunoglobulin preparations which do not contain any procoagulants.

The protease effect may often result in a homomeric and heteromeric formation of aggregates, which may even cause a visible formation of particles from insoluble aggregates, increases in viscosity, a deceleration of the necessary filtration steps, decreased yields and an unsatisfactory stability during the storage of intermediate and finished products.

The problem arises from the necessity to prevent, as far as possible, the formation of proteases and their effects on therapeutic proteins during the manufacture and storage thereof so that unsatisfactory yields during the necessary purification processes as well as reductions in quality as a result of changes in their molecular structure caused by enzymatic processes are avoided. Therefore, it is necessary to implement manufacturing processes that allow for a recovery and reprocessing of the starting material without resulting in enzyme-mediated changes in the therapeutic proteins during the required purification process, including the removal of viruses.

Thus, it is necessary that, during manufacture and storage, the therapeutic proteins are protected by an appropriate cleansing and/or the addition of enzyme inhibitors from all direct effects of enzymes which recognize them as substrates as well as from any indirect effects caused by proenzymes, cofactors and procofactors.

It is also necessary to determine the enzyme concentrations which do not yet lead to modifications in a particular therapeutic protein, taking into consideration the exposure time and other conditions important for the enzymatic activity.

For the stability of therapeutic proteins, it is necessary to measure enzyme activities over lengthy periods of time in order to be able to infer the long-term stability from the accelerated stability test. Such accelerated stability tests usually last for a period of at least one month.

Since even very small enzyme amounts may lead to modifications in therapeutic proteins, the development of appropriate determination methods lasting for fairly long amounts of time is necessary.

It is also important to measure the inhibitor amount which is required for inhibiting unremovable proteases and for maintaining said inhibition in the long run.

3. SUMMARY OF THE INVENTION

The invention relates to storable medicaments produced from pharmaceutical active ingredient preparations which are virus safe. Said medicaments contain at least one intact therapeutic protein obtained from plasma or by means of genetic engineering, as an active pharmaceutical substance. Said active ingredient preparations contain active enzymes, especially proteases, which are either free or bound to the substrates thereof and cat against the therapeutic protein(s) present.

The invention thus relates to storable drug compositions produced from virus-safe, pharmaceutical drug substance preparations and containing one or more intact therapeutic proteins obtained from plasma or by means of genetic engineering and acting as the active pharmaceutical substance or substances, respectively, wherein neither any free active enzymes, in particular proteases, nor such that are bound to their substrates are present in the drug substance preparations at concentrations which reduce the safety or effectiveness of a therapeutic protein or of therapeutic proteins.

4. DETAILED DESCRIPTION OF THE INVENTION

If therapeutic proteins are zymogens, they must not contain any proteases or activatable enzyme cascades which activate zymogens to proteases.

If possible, therapeutic proteins should not contain any proenzymes which may be activated to enzymes which recognize therapeutic proteins as substrates, neither should they contain any cofactors and procofactors promoting said activation.

The solution to the problem is thus achieved by consistently meeting the conditions of manufacture and storage, wherein the effects of one enzyme or several enzymes on therapeutic proteins, which are their substrates, are largely prevented, just as the formation of such enzymes from their respective proenzymes.

In order to prevent enzyme-mediated modifications in starting materials, intermediates and final products, it is necessary to determine minor activities of proteases which do not yet lead to modifications in active therapeutic proteins. For this purpose, determination methods are required which are even capable of detecting traces of enzymes. By way of Example 11 of the ultrasensitive determination of thrombin, it is shown that, via a long-term incubation with chromogenic substrates, even thrombin amounts as small as from 30 to 100 µU/millilitre are still detectable. This corresponds to a 300-1000 picomolar solution of thrombin and an amount of 300 to 1000 allomoles/mL.

According to the invention, the control of a certain enzyme activity is carried out such that a sensitive, low-molecular substrate is selected for the protease to be determined and, during the entire manufacturing process, a parallel sample is subjected to the same manufacturing conditions and the enzymatic cleavage of the substrate in said sample is measured. The low-molecular substrates used in the parallel samples must have a stability which is as high as possible so that they can be used in long-term tests. Suitable chromogenic or fluorogenic substrates must be selected which are cleaved to the utmost extent by the protease to be examined. The amounts of a cleaved substrate formed during the manufacture, interim storage and storage of a therapeutic protein can be detected in catal equivalents and based on the weight or the activity of a therapeutic protein. See Example 9.

Furthermore, the invention relates to purification processes for the recovery of therapeutic proteins from blood or biomasses. The auxiliary materials required therefor can be removed completely or partially from the obtained drug substances at the end of the manufacturing process. Via the extensive elimination of protease activities, the manufacturing process is performed such that at least 60%, preferably 95%, of the respective therapeutic protein, based on the starting material, can be recovered.

According to the invention, also atoxic, chaotropic substances may additionally be used, which chaotropic substances dissociate an enzyme-substrate bond or prevent such a bond from forming, respectively, and hence improve the separation of enzymes, in particular proteases, which are bound to therapeutic proteins, the chaotropic substances being removed after the separation process.

By consistently maintaining low temperatures of between 0° C. and 4° C., complexing of calcium ions, the application of certain inorganic and organic substances as well as chaotropic agents, the adjustment of redox potentials and the application of suitable dissolved or immobilized enzyme inhibitors, enzyme activities are kept as low as possible. If soluble, high-molecular enzyme inhibitors are used, it must be ensured that they are atoxic and virus-safe and, at the concentrations used, do not influence the effect of therapeutic proteins. See Example 10.

Still present residual activities of enzymes are measured during the entire manufacturing process in samples of all intermediates by the addition of sensitive, low-molecular substrates for the individual enzymes to be traced. If, at a certain intermediate stage, the enzyme activity exceeds the predetermined minimum limits, the concentration of the used inhibitor or of the used inhibitors, respectively, shall be increased immediately. See Example 13.

In manufacturing steps in which enzyme activities still present interfere, suitable dissolved or immobilized enzyme inhibitors are added in the necessary amounts. Dissolved allogenic inhibitors are removed or used as a drug substance, together with the therapeutic protein.

During the production of therapeutic proteins it is necessary to carry out virus inactivations and virus depletions which, in most cases, have to be performed at room temperature or at slightly higher temperatures. Upon completion of the virus inactivation process, virucidal chemicals are separated from the therapeutic proteins. The virus depletion of therapeutic proteins may be performed, for example, by nanofiltration at temperatures ranging between 20° and 40° C., whereby nanofilters having pore sizes of 75 nm and 35 nm are used. In order to achieve a safe depletion of all viruses, it is necessary to use a 20 nm pore filter and subsequently a 15 nm pore filter. Since said process steps must be performed at temperatures between 20° C. and 40° C., undesired enzyme activities have to be reduced appropriately by the addition of suitable inhibitors. See Example 10.

During the storage of citrate plasma, various proteolytic activities increase strongly despite low storage temperatures of −20° C. Such strongly increased enzyme activities are detectable also in the cryoprecipitate and cryoprecipitate supernatant produced from said plasma, as shown in Example 1. By adding EDTA to freshly recovered citrate plasma, the calcium ion activity measured by means of a calcium electrode can be prevented virtually completely. By said addition, the formation of proteolytic enzymes can be prevented if the plasma is stored in the deep-frozen state. If cryoprecipitate paste produced from freshly recovered plasma is stored in the deep-frozen state, an activation of proteases occurs. The formation of proteolytic enzymes can be prevented by adding EDTA prior to the freezing of the cryoprecipitate. If a cryoprecipitate supernatant is reprocessed immediately, it is not necessary to add any further EDTA. If it is desired to store the cryoprecipitate supernatant in the deep-frozen state, the formation of proteases can be prevented by adding small amounts of heparin prior to freezing. See Example 1.

The invention also relates to a virus-safe fibrinogen as an active pharmaceutical substance in drug compositions, which fibrinogen is characterized in that it exhibits less than 4% fibrin monomer complexes, based on the total protein (fibrinogen and fibrinogen monomer complexes), and less than 1 µU of thrombin per mg fibrinogen. See Example 2.

A fibrinogen-containing drug composition storable in the liquid state at refrigerator temperature is also according to the invention, which drug composition is characterized in that it has a thrombin activity of less than 1 µU of thrombin per mg fibrinogen and contains arginine as a chaotropic agent at a concentration of from 0.5% to 5.0%. If fibrinogen is produced from plasma which has been stored at −20° C. for a lengthy period of time, it may contain 5% fibrin monomer complexes or more. If stored in a refrigerator, this leads to gelatinization. Depending on the content of fibrin monomer complexes, said gelatinization can be prevented by adding chaotropic agents such as arginine. See Example 3.

Thrombin is used as such or together with fibrinogen for stopping bleeding, since, used at sufficient concentrations, it immediately results in the formation of a haemostatic plug. Thrombin preparations may be contaminated with plasmin, and such preparations, combined with fibrinogen, also lead to the formation of a haemostatic plug, however, said plug disintegrates more or less quickly due to the presence of plasmin, whereby the bleeding which has been stopped might restart. As shown in Example 4, as a result of the cleansing of plasminogen and plasmin, it is possible to produce a thrombin preparation which is free from fibrinolytic properties.

Immunoglobulin G, which can be stored as a finished pharmaceutical preparation both in a freeze-dried and in a liquid state, is basically used for curing an antibody deficiency in patients suffering from an antibody deficiency syndrome and recently also for various severe inflammatory diseases, in particular in neurology. The dosage in case of such inflammatory diseases may amount to up to ten times the amount used for immunodeficiency diseases. This high-dose treatment with immunoglobulin G can involve side effects which are caused by peripheral, coronary or cerebral vascular occlusions. For this reason, immunoglobulin preparations should be largely free from procoagulants. Immunoglobulin preparations are generally contaminated by factors of the contact phase such as callicrein and activated Clotting Factor XI. By adding $C_1$-inhibitor and heparin, these enzyme activities can be largely reduced or rendered undetectable, respectively. See Example 5.

Furthermore, the effect of proteases, particularly plasmin, on immunoglobulins may cause a cleavage into the Fab-fragment and the Fc-piece. This is accompanied by a strong decrease in the biological activity, caused by an extensive temporal shortening of the biological availability and a reduction in the quality of the antibodies contained in the immunoglobulin G preparation. During the manufacture and storage of the product, plasmin forms from the plasminogen contained in most immunoglobulin preparations. By adding dissolved or immobilized inhibitors such as aprotinine, the plasmin formation as well as the effect of plasmin can be prevented.

As a result of a repeated salt precipitation in the presence of urea, it is possible to separate fibrinolytic activities to such an extent that, with repeated precipitations in the immunoglobulin preparation, a fibrinolysis is no longer detectable. See Example 5.

Furthermore, the invention relates to a virus-safe Factor VIII-preparation which is characterized in that it has no detectable thrombin activity and an antithrombin content of less than 10 arbitrary antithrombin units per unit of Factor VIII and that not more than 0.2 units of Factor VIIIa are contained per unit of Factor VIII.

The prothrombin complex consists of four zymogens, Clotting Factors II, VII, IX and X. Their formation in the organism depends on Vitamin K. By Vitamin K antagonists such as warfarin, the formation of these clotting factors can be reduced in a dose-dependent way, rendering possible an oral anticoagulant treatment at a desired intensity. Said treatment is necessary for preventing imminent vascular occlusions. If necessary, the oral anticoagulant treatment can be suspended immediately by the parenteral administration of prothrombin complex. With patients whose basic disease leads to a prothrombin complex deficiency, a tendency to bleed can also be eliminated immediately by the parenteral supply of prothrombin complex.

Sometimes, severe side effects as a result of vascular occlusions caused by thrombus formation occur in a parenteral treatment with prothrombin complex preparations. Such vascular occlusions are attributed to activated clotting factors which may be contained in prothrombin complexes. The activation of the clotting factors contained in the prothrombin complex is triggered by the activated Clotting Factor Xa which leads to the formation of thrombin from prothrombin and subsequently to the formation of fibrin from fibrinogen. The activation of Factor Xa may occur both via the extrinsic tenase pathway, which depends on Clotting Factor VIIa, and, to a larger extent, via the intrinsic tenase pathway, which depends on the activated Clotting Factors IX and VIII.

According to the invention, the formation of Factor Xa via the intrinsic tenase pathway is achieved by a complete cleansing of Clotting Factors VIII and VIIIa from the prothrombin complex. By obtaining an as high as possible content of plasmatic TFPI in the prothrombin complex preparation, the formation of Factor Xa via the extrinsic tenase pathway is stopped. See Example 7.

As shown in Example 9, it is possible to detect and determine proteolytic enzymes at extremely low concentrations via a 100- to 1000-fold prolongation of the incubation times of an enzyme with a chromogenic substrate. By choosing stable chromogenic substrates, it is possible to detect and determine the effect of proteases also at low temperatures close to the freezing point, using incubation times that are 1000 to 10000 times longer than the normal incubation time of three minutes. Said cleavage of chromogenic substrates over a prolonged period of time is not even reduced in the presence of the natural high-molecular substrates of the enzymes.

Enzymatic conversion products which are caused by enzymes at concentrations ranging from micromolar to femtomolar may be detected or determined in therapeutic proteins produced according to the invention by mass spectrometry, HPLC, gel filtration, and chromatographic, electrophoretic or immunologic methods. See Example 12.

The enzyme activities can be determined by means of samples for process control by maintaining a chosen chromogenic substrate concentration throughout the entire manufacturing process, if necessary, by the addition of a supplementary chromogenic substrate. The enzymatically cleaved chromogenic substrate is calculated as the difference between the total amount of cleaved chromogenic substrate less the substrate in corresponding controls. If chromogenic substrates containing p-nitroaniline are used, the absolute amount of the cleaved chromogenic substrate is evaluated by means of a p-nitroaniline calibration curve.

In order to achieve optimum storage conditions for drug compositions containing therapeutic proteins, the addition of enzyme inhibitors may be required during the formulation of the drug composition. During the application of such drug compositions lasting for several hours, the liquid drug composition must have a sufficient stability at room temperature. If the drug composition is consumed only partially and the unconsumed drug composition is stored in the refrigerator, stability must be ensured for about three days at refrigerator temperature. See Example 8.

5. WORKING EXAMPLES

Preferred embodiments of the invention are explained in more detail by way of the following examples.

1. Recovery of a Protease-Depleted Starting Material and of Crude Fractions Produced Therefrom for the Production of Therapeutic Proteins:

A. Protease-Depleted Plasma:

Fresh citrate plasma with a content of not more than 300 µU of thrombin per mL is mixed with as much of a 1% EDTA solution so that the calcium ion activity does not exceed the ion activity of a 10 µM calcium chloride solution. Measurements were conducted by means of a calcium electrode Type 15 220 3000 of Messrs. Mettler Toledo. The measuring chain voltage was read off in mV, and a calibration curve was established in the upper and lower measuring ranges at 25° C. If EDTA is added, the complex bond of calcium ions by EDTA is measured by reducing the measuring chain voltage. Measuring chain voltages below −15 mV were not taken into account. As the lowest measuring range, measuring chain voltages corresponding to a 5-10 µM calcium chloride solution were not taken into account. The plasma mixed with EDTA solution is also frozen, the calcium ion activity in defrosted samples is determined at intervals of 30 days and likewise the thrombin and thrombin-like activities with the chromogenic substrate S-2238. There is no significant increase in the enzyme activity in the plasma mixed with EDTA, while the thrombin and thrombin-like enzyme activities increase further in the stored citrate plasma which was not mixed with EDTA, amounting to 5-10 times the initial value after three months of storage at −20° C.

Fresh plasma mixed with EDTA until a measuring chain voltage of 15 mV has been reached has not more than 1000 µU of thrombin per mL after three months of storage at −20° C. The determination of the thrombin activity is performed with the chromogenic substrate S-2238, whereby, in this case, both the thrombin and thrombin-like enzyme activities are measured and expressed in units of thrombin.

B. Protease-Depleted Stored Cryoprecipitate:

From the plasma mixed with EDTA which is stored in the deep-frozen state, during defrosting at a temperature not exceeding 5° C., a precipitate thus formed, the cryoprecipitate, can be recovered by centrifugation at between 10000 and 20000 rpm. The sediment is stirred to form a readily liquid pulp by adding a 0.1% citrate solution, wherein the temperature should amount to between 2° C. and 4° C., and may be used in this form for the further production of fibrinogen, Factor VIII, Factor V and Factor XIII. If storage is desired, a 1% EDTA solution is added to said pulpy suspension under stirring until a sample taken therefrom, diluted 10 times with distilled water, corresponds to the calcium ion activity of a 10 µM calcium chloride solution. The EDTA-containing pulpy suspension thus obtained is then frozen and stored at −20° C. or at lower temperatures. After defrosting the cryoprecipitate suspension within three months, the thrombin activity in a solution which does not contain more than 3 mg fibrinogen per mL, which activity is measured with the chromogenic substrate S-2238, amounts to 1000 µU of thrombin per mL.

C. Protease-Depleted Cryoprecipitate Supernatant:

The supernatant obtained after centrifuging the cryoprecipitate can, as such, be processed further immediately. If a storage in the deep-frozen state is planned, any present protease activities are minimized by the addition of 1 U of heparin per mL cryoprecipitate supernatant. If a storage period of six months in the deep-frozen state is planned, the cryoprecipitate supernatant mixed with heparin must not contain more than 1 ng of Factor XIa, 100 U of callicrein, 1 mU of Factor Xa, 10 mU of thrombin and 100 mU of plasmin per mL.

2. Production of Thrombin-Free Fibrinogen:

Under stirring for one hour, about 650 g of a cryoprecipitate paste obtained from 100 L of human blood plasma is dissolved in 10 L of a 0.1% sodium citrate solution at a temperature of from 2° to 4° C. while a pH-value of between 7.0 and 7.5 is maintained. The dissolution of the cryoprecipitate is not performed entirely. After sample taking, the total weight of the solution is determined and the entire solution is frozen and stored at −20° C.

In the sample drawn, the contents of fibrinogen and fibrinopeptide A are determined. Likewise, the thrombin activity is measured at 4° C. and 37° C. with the aid of the chromogenic substrate S-2238. The fibrinogen content is determined nephelometrically and the fibrinopeptide A content is determined quantitatively by means of an Elisa method.

In case the determination of thrombin at 37° C. results in a thrombin activity of more than 10 µU of thrombin/mL fibrinogen, a calculated amount of r-hirudin (lepirudin) is added after the defrosting of the main quantity, which calculated amount is derived from an amount of r-hirudin measured in a preliminary test and necessary for setting the thrombin activity at or below 10 µU of thrombin/mg fibrinogen. The defrosted cryoprecipitate solution is mixed with 150 g of glycine per kg cryoprecipitate solution at a temperature not exceeding 5° C. and is stirred for 30 minutes. The fibrinogen thus precipitated is separated by centrifugation in a Sharples centrifuge after a storage period of from 12 to 24 hours at from 2° C. to 4° C. The throughput time is adjusted such that a clear, precipitate-free supernatant is obtained. The supernatant can be frozen for further processing and can be stored at −20° C. In a sample of the supernatant, any still existing fibrinogen, fibrinopeptide A, thrombin activity and thrombin activity inhibition are determined.

The sediment obtained by glycine precipitation and centrifugation is dissolved in a 0.1% citrate buffer having a pH of from 7.0 to 7.5, the fibrinogen content is determined nephelometrically and is adjusted to a desired fibrinogen concentration of between 1% and 2% by the addition of more citrate buffer. Dissolution in a citrate buffer is carried out at a temperature of from 2° C. to 4° C. just as the subsequent centrifugation of the dissolved glycine precipitate at from 10000 to 15000 revolutions per minute and for a centrifugation period of at least 10 minutes. The sediment obtained by centrifugation is discarded, and the supernatant is mixed with ⅒ of the originally added amount of r-hirudin and is adjusted to a glycine concentration of 15% by the addition of solid glycine. The pH-value of the suspension should not fall below a pH of 6.5, nor should it exceed a pH of 7.5. Any corrections to the pH-value that are necessary are carried out by using a 1% citric acid solution or a 0.1% caustic soda solution. Upon being left to stand at from 2° C. to 4° C. for a duration of from 12 to 24 hours, the precipitate is centrifugated, and the obtained fibrinogen sediment is dissolved in a 0.1% citrate solution at a pH of from 7.0 to 7.5. In case the solution contains more than 1 µU of thrombin per mg fibrinogen, a further amount of r-hirudin is added in order to settle the thrombin activity at below 1 µU of thrombin per mg fibrinogen. The reprecipitation of the fibrinogen by means of glycine and the possibly required addition of r-hirudin may also be repeated several times in order to achieve sufficient purification of the fibrinogen.

A sufficiently purified fibrinogen is provided if at least 95% of the present protein clots due to the addition of thrombin, the fibrinogen peak of gel filtration involving Superose 6HR 10/30, Amersham, amounts to at least 94% and a product with clean bands is provided if 10 µg of fibrinogen is applied during the SDS gel electrophoresis. Furthermore, fibrinogen bands must not occur when using a reducing buffer, and three bands of the respective fibrinogen chains have to appear.

The fibrinogen solution thus obtained may be freed from any excess precipitant by diafiltration against a 0.1% citrate, and, after virus inactivation has been completed, also from trinitrobutylphosphate and Tween-80. Since both diafiltration and virus inactivation are performed with a solvent/detergent and, if necessary, a subsequent nanofiltration is carried out at room temperature, it is perhaps necessary to add further amounts of r-hirudin such as to prevent the thrombin activity from rising above 1 µU of thrombin per mg fibrinogen during those manufacturing stages.

The virus-inactivated and virus-depleted fibrinogen solution may be stored in the deep-frozen or lyophilized state until further processing. Upon the defrosting or reconstitution, respectively, of the lyophilized fibrinogen in a suitable solvent, formulation, sterile filtration, portioning and filling into units for the ultimate user may be carried out. The finished drug composition thus produced may be stored both in the liquid or frozen and in the lyophilized states.

The integrity of the fibrinogen thus obtained and processed to a finished drug composition is determined by the amount of fibrinopeptide A that is formed during the entire manufacturing and storage periods. The total amount of fibrinopeptide A, based on the total initial amount of fibrinogen, must not exceed 10% and should preferably be 5%.

3. Production of Fibrinogen-Containing Solutions which do not Lead to Gelatinization at Temperatures of Between 0° C. and 5° C.:

Fibrinogen produced according to conventional methods contains between 5% and 15% fibrin monomer complexes. The exact determination of the fibrin monomer complexes is performed via gel filtration and, according to the invention, by the addition of 5% urea to the fibrinogen-containing solution to be examined. As a result of the chaotropic effect of the urea, a proper separation of fibrin monomer complexes and fibrin is achieved.

A fibrinogen solution containing between 1% and 10% fibrinogen is mixed with different amounts of solid arginine so that fibrinogen solutions are formed which contain 0.5%, 1%, 2%, 4% and 8% arginine. As a control, a fibrinogen solution without added arginine is carried along. The arginine solutions and the control are maintained at room temperature for at least 15 minutes and are then brought to a temperature of between 0° C. and 5° C. After an incubation period of up to 24 hours, the amount of arginine which must be added to prevent gelatinization is determined.

Said procedure is used for the production of a drug substance preparation containing fibrinogen as a therapeutic protein as well as in the formulation of fibrinogen-containing drug compositions, in particular if they are stored in the liquid state. However, the calculated amount of arginine may also be added prior to the deep-freezing of fibrinogen-containing drug compositions in order to prevent gelatinization during a refrigerator storage after the defrosting or reconstitution, respectively, with solvents.

4. Recovery of Fibrinolysis-Free Thrombin Solutions:

Thrombin, manufactured by the activation of prothrombin according to any method, is absorbed several times (at least five times) on CM-sepharose and is eluted with a sodium chloride gradient buffered with a 10 mM phosphate solution, pH 7.0, between 120 and 180 mM sodium chloride solution. Prior to the elution, the thrombin-containing CM-sepharose is washed five times with 10 times the amount of its volume, wherein a wash solution having a 10 mM sodium phosphate content and a 50 mM sodium chloride content at pH 7.5 is used and the washing process is carried out at between 2° and 4° C.

The thrombin eluted with between 120 and 180 M sodium chloride is tested for its content of plasmin and with t-PA-activatable plasminogen. The examination is conducted in the fibrinolysis test. 100 µL of the eluate, which was adjusted to about 100 U of thrombin per mL, is mixed with 50 µL of a 0.025 molar calcium chloride solution and 100 µL of a 1% plasminogen-free fibrinogen solution. Said batch is prompted to clot in a cuvette, and an emerging lysis is monitored with an Elisa-Reader Sunrise TECAN for 18 hours. A simultaneous batch which, in addition, contains 10 mU of t-PA is also tested for its lysis period. In both batches, the thrombin solution to be examined must not cause lysis after 18 hours.

If lysis is observed, the above-described purification of thrombin on CM-sepharose must be carried out until no lysis of the batch can be observed for up to 18 hours in the fibrinolysis test.

5. Production of Stable, Harmless, Functionally and Structurally Intact Immunoglobulin G Preparations:

Cohn-Fraction II, upon removal of alcohol by lyophilization or diafiltration, is brought to a content of 1-2% protein by dissolution in distilled water. Said solution is mixed with <50 g urea per L, adjusted to pH 8 with 0.1% caustic soda, and sodium sulphate is added in such amounts until a saturated sodium sulphate solution is formed. The precipitate-containing sodium sulphate solution is decanted from a possible undissolved excess amount of sodium sulphate, and the precipitated immunoglobulin is recovered by centrifugation with the aid of a continuous centrifuge. During the entire procedure, the pH value should lie between 7.5 and 8.0. After the centrifugation, the immunoglobulin precipitate obtained by sodium sulphate saturation is dissolved in distilled water, using the amount of water which results in a roughly 5% immunoglobulin solution. Said immunoglobulin solution is tested for its amount of plasminogen capable of activating plasmin and tPA or urokinase. For this purpose, 500 µL of said solution is mixed with 10 U of tPA or urokinase in a volume of 50 μL, and 50 μL stimulator containing 1% fibrinopeptides is added. After the addition of 100 μL of a 4 mM chromogenic substrate solution S-2403, the batch is incubated at 37° C. and the amount of p-nitroaniline is determined photometrically. By means of the obtained ΔA, the content of plasmin units is determined on a standard calibration curve, which content must not exceed 0.1 Upper mL of a 5% immunoglobulin solution. Said amount of plasmin thus determined is composed of amounts of plasmin which are already present and of those formed by plasminogen activators.

Moreover, the diafiltrated immunoglobulin solution must not contain more than 10 U of callicrein and not more than 1 ng Clotting Factor XIa, based on a 5% immunoglobulin solution. The content of callicrein is determined with the chromogenic substrate S-2302 and the content of Factor XIa is determined with the chromogenic substrate S-2366.

In order to eliminate any procuagulant effects of the obtained immunoglobulin G preparation, it is determined whether there is a shortening of the clotting time of a recalcified citrate plasma. For this purpose, 100 μL citrate plasma is properly mixed with 100 μL of the immunoglobulin preparation to be examined having a protein content of 5%, and 100 μL of a 25 mM calcium chloride solution is added and the clotting time is measured at 37° C. A batch of 100 μL citrate plasma with 100 μL buffer serves as a control, to which 100 μL of a mM calcium chloride solution is added after thorough mixing and for which the clotting time is determined in the same manner. The clotting times measured depending on the used citrate plasma should be between 300 and 500 seconds. The shortening of the clotting time by a 5% immunoglobulin should amount to less than 10%.

6. Preparation of a Factor VIII-Concentrate that is Free from Factor VIIIa:

A deep-frozen sample of the supernatant of the 15% glycine precipitate of the dissolved cryoprecipitate, which supernatant is stored in the deep-frozen state, is tested after being defrosted for the entire existing activity of Factor VIII which is composed of the existing Factors VIII and VIIIa by the aid of the Factor VIII Chromogen Kit, DADE Behring. The determination is performed with and without the addition of the thrombin provided in the kit. The difference which results from the two determinations is evaluated as the amount of Factor VIII which can be converted to Factor VIIIa by means of thrombin.

In the sample, the amount of the existing thrombin inhibitor also is determined in arbitrary inhibitor units. In case less than 10 arbitrary inhibitor units per U of Factor VIII are provided in the tested sample, the inhibitor content is increased accordingly by the addition of r-hirudin.

By ultrafiltration using a 30 K or 50 K Dalton filter, 5 mL of the sample is largely freed from glycine by washing with a 25 mM phosphate buffer containing 0.1% of citrate and having a pH of 7.3, and the retentate is tested for Factor VIII-cleavage products. By electrophoretically separating the proteins into a 5% acrylamide gel and a 10% separating gel, the blotted protein bands are tested for any possibly existing cleavage products by the aid of a monoclonal antibody against the heavy chain of Factor VIII.

The frozen main quantity of the glycine supernatant of Example 2 is mixed with 350 g of β-alanine per kg supernatant under stirring at from 2° C. to 4° C. The precipitate containing the main quantity of Factor VIII is obtained by centrifugation at a rotational speed of between 10000 and 15000 revolutions per minute after being left to stand at from 2° C. to 4° C. for a duration of from 12 to 24 hours, whereby such a flow rate is chosen that a clear supernatant results. The Factor VIII-containing sediment is dissolved in an amount of 0.1% citrate buffer having a pH of 7.5 such that per mL a Factor VIII content of between 50 and 500 U results. The entire procedure is carried out at a temperature of between 2° C. and 4° C. After measuring the amount of thrombin inhibitor, if necessary, the ratio between Factor VIII and inhibitor is adjusted to 10 arbitrary thrombin inhibitor units per 1 U of Factor VIII by the addition of r-hirudin. At room temperature, the solution is then largely freed from glycine and β-alanine by diafiltration against a 0.1% citrate solution having a pH of from 7.0 to 7.5, whereby, prior to diafiltration, it may be further purified by one or two reprecipitations with β-alanine with respect to Factor VIII. At room temperature, further purification steps may be carried out by chromatography using weak anion exchangers. Likewise, the virus inactivation involving a solvent/detergent and a subsequent multi-stage nanofiltration at between 25° C. and 30° C. may take place.

If desired, an increase in the Factor VIII-concentration is achieved by diafiltration. The Factor VIII-concentrate that is obtained may be deep-frozen or stored temporarily after lyophilization. The defrosted frozen solution or the reconstituted lyophilized powder, respectively, is formulated, sterilized by filtration, bottled batchwisely and subjected to another lyophilization in the filled flacons. At least 80% of the existing Factor VIII-activity must be provided as the intact Factor VIII, up to 20% of the activity may be caused by Factor VIIIa. In a solution containing 100 U of Factor VIII, there must not be any thrombin activity, whereby a determination method is used with the aid of which even 30 μU of thrombin per mL can be determined.

7. Prothrombin Complex Preparations that are Free from Activated Clotting Factors:

1 L of cryoprecipitate supernatant is mixed with 16 g A-50, a weak anion exchanger, is stirred at room temperature for 15 minutes, and the ion exchanger, which has absorbed Clotting Factors II, VII, IX and X contained in the cryosupernatant by 90% or more, is separated by centrifugation. The supernatant containing the main quantity of the albumin contained in the plasma and of the immunoglobulins contained therein, respectively, is fractionated further in order to recover inhibitors, immunoglobulins and albumin.

The separated A-50 anion exchanger is washed extensively three times with 5 L of 150 mM sodium chloride solution in each case, at temperatures of between 2° C. and 4° C., and then the prothrombin complex consisting of Clotting Factors II, VII and X and also the main quantity of the Tissue factor pathway inhibitor (TFPI) contained in the cryosupernatant are eluted by the aid of a 500 mM sodium chloride solution. The processes of absorption and elution of the weak anion exchanger A-50 are repeated until, in a Factor Xa generation test, no Factor VIII is detectable per 10 U of prothrombin. The prothrombin determination is conducted by means of ecarin and by measuring the formed meizothrombin and thrombin with the chromogenic substrate S-2238. The TFPI is determined by measuring the inhibition of the Factor-Xa activity. At least 0.2 U of TFPI must be provided per 1 U of prothrombin.

8. Stabilized Therapeutic Proteins in Drug Compositions:

Prior to the formulation of drug substance preparations containing therapeutic proteins, it is determined by formulating a sample whether it is still possible to detect activities of proteases which destroy functions or structures of therapeutic proteins. If cleansing is incomplete during the purification process of therapeutic proteins, atoxic, virus-safe, high-molecular protease inhibitors must be added during the formulation of drug compositions, which protease inhibitors inactivate proteases to such an extent that they do not lead to a loss in effectiveness and safety of the drug composition. On the other hand, the added inhibitor amounts must not reduce the effectiveness of a therapeutic protein. The addition of non-toxic, high-molecular protease inhibitors such as antithrombin III and $C_1$-inhibitor, alone or together, is advantageously carried out with unfractionated heparin or HMW heparin. The amount of inhibitors to be added is determined by the required minimization of enzyme activities. Drug substance preparations containing therapeutic proteins are tested for their cleavage by proteases with the chromogenic substrates S-2238, S-2302, S-2366, S-2403 and S-2765. In case of excessively high protease activities, appropriate inhibitors are added in order to bring about the required decrease in the enzyme activity. If the preliminary tests show that enzyme amounts which can no longer be detected clearly with chromogenic substrates already cause a decrease in the activity, safety and stability of drug compositions containing therapeutic proteins, especially in case of lengthy storage periods, the determinations of activity are conducted with the appropriate fluorogenic substrates which are up to 100 times more sensitive than chromogenic substrates.

The required additions of enzyme inhibitors are evaluated in a concentration series. Samples of the drug composition to be formulated are mixed with enzyme inhibitors in a geometrical concentration series and, of each chromogenic substrate, 100 nm is added, based on 1 mL of the ready-to-use drug composition. Depending on the requirements, said batches can be freeze-dried, deep-frozen or stored in the liquid state at refrigerator temperature, respectively. After three months of storage at predetermined temperatures, the deep-frozen and freeze-dried batches are defrosted and reconstituted, respectively, and the amounts of p-nitroaniline formed in all three batch series are determined photometrically. In respective control batches which only contain chromogenic substrates dissolved in buffer at a concentration of 100 μM and which were prepared and stored in the same way as the samples, the amount of the formed p-nitroaniline is likewise determined, and these amounts are subtracted from the calculated values of the sample batches. The batches with sufficient addition of inhibitor as well as those with higher inhibitor concentrations and their controls are stored for another three days at refrigerator temperature and for 20 hours at 25° C. The amounts of inhibitor or inhibitors, respectively, which prevent further p-nitroaniline from forming are evaluated.

The amount of p-nitroaniline formed after 24 hours of incubation at 37° C. must not amount to more than 100 nm p-nitroaniline if the chromogenic substrate S-2238 is used per mL of the ready-to-use drug composition, and must not amount to more than 200 nm if S-2302 is used at the same concentration, and must not amount to more than 50 nm in case of the chromogenic substrate S-2366, and must not amount to more than 100 nm in case of the chromogenic substrate S-2403, and must not amount to more than 100 nm in case of the chromogenic substrate S-2765. The corresponding batches contain the chromogenic substrates in an amount of 200 nm per mL. The starting, intermediate and final products to be examined are added in such amounts that, after 24 hours of incubation at 37° C. and a layer thickness of 10 mm, no absorbance value greater than 1.000 is read off the photometer.

9. Process Controls During the Production of Therapeutic Proteins and Quality Controls of Drug Substance Preparations Containing Therapeutic Proteins:

The enzyme activities occurring during the production of therapeutic proteins result from the starting material as well as from proteases which are formed from zymogens during the manufacturing process. In consideration of the protease amounts located in the starting material, the entire manufacturing process is monitored in terms of the activation of zymogens to proteases, the cleansing of such proteases and in terms of protease activities still remaining in the therapeutic proteins. Thrombin, callicrein, Factor XIa, plasmin and Factor Xa as well as thrombin-like, callicrein-like, Factor XIa-like, plasmin-like and Factor Xa-like protease activities are measured with the chromogenic substrates S-2238, S-2302, S-2366, S-2403 and S-2765. All high-molecular substances located in the starting material, which are separated from the therapeutic proteins in the course of the production, are collected and deep-frozen immediately. At the end of the manufacturing process, the collected, deep-frozen residues are defrosted, pooled and tested for enzyme activities with the aid of the five chromogenic substrates. In connection with the enyzme content of the starting material, it is possible to estimate to what extent the activation of proenzymes occurred during the manufacturing process. If, during the production of therapeutic proteins, the suspicion arises that the presence of the activated Clotting Factors VII and IX could directly or indirectly lead to proteolytic effects on a particular therapeutic protein, additional determinations of such enyzme activities are conducted with Spectrozymes VIIa and IXa (American Diagnostics). In case of therapeutic proteins which react with great sensitivity to protease effects, such as Factor VIII, fluorogenic substrates instead of chromogenic substrates can be used for increasing the sensitivity.

The amount of a particular protease present in a sample is determined by the aid of a calibration curve. The calibration curves for thrombin were established with the NIBSC Standard 89/580, for callicrein with Coachrom Humankallikrein 0.01 U/mL. The calibration curve for Factor XIa was established with a Factor XIa concentrate from American Diagnostics, wherein 260 ng Factor XIa normalize the clotting time of a plasma lacking Factor XI by 50%. For plasmin, the $3^{rd}$ International Standard 1998 of NIBSC 97/536 was used, for Factor Xa, a reference preparation of NIBSC was used. For the standarization of the Factor XIa preparation, it was furthermore noted down which amount of Factor XIa, expressed in ng, corresponds to the amount of Factor XI which normalizes a plasma lacking Factor XI by 50% within its clotting time.

If a respective necessary reduction in protease activities is not achievable by antithrombin III, $C_1$-inhibitor and heparin or a combination thereof, the following inhibitors, alone or together, can be used with antithrombin III, $C_1$-inhibitor and heparin: aprotinine, inter-α-trypsin inhibitor, plasma antiplasmin, plasma anti-trypsin and Tissue factor pathway inhibitor. All those inhibitors must be virus-safe.

Drug substance preparations containing active pharmaceutical substances (ICH: drug substances) are preformulated such that, with an appropriate storage, their activity, harmlessness and stability is maintained for weeks or months. The required quality controls refer essentially to the complete conservation of the pharmaceutical activity and to the lack in procoagulation activity. In order to determine the maximum storage period for a drug substance preparation, the period of time is determined in which no decrease in pharmaceutical activity, no measurable increase in protease activity and no shortening of the plasma prothrombin time, the plasma aPTT and the plasma recalcification time by more than 10% occur yet. If drug substance preparations are stored in the deep-frozen state and their storage life expires too soon, the storage life can be increased substantially by lyophilization and, if required, storage of the freeze-dried drug substance at −20° C.

10. Separation of Enzymes and Viruses as Well as Inactivation of Viruses and Inhibition of Enzymes in Additional Manufacturing Steps:

In various manufacturing processes of therapeutic proteins, an activation of one or more proenzymes may occur. Such enzymes are able to cause lasting changes in therapeutic proteins. The effect of some enzymes can depend strongly on the redox potential. In order to prevent the stimulating effect of Factor XIIIa on the formation of fibrin monomer complexes, the enzymatic activity of Factor XIIIa can be largely reduced by the addition of cystine. On the other hand, the activity of Factor XIII is strongly increased by cysteine and other reducing agents. Since Factor XIII may cause an increase in the formation of fibrin monomer complexes even at low concentrations, an adequate sensitive determination method is necessary.

In order to remove Factor XIII and Factor XIIIa, the thrombin-free fibrinogen produced according to Example 2 is mixed with cystine in an approx. 1% solution until the cystine concentration reaches a molarity of 50 mM. Fibrinogen is precipitated from said solution by the addition of glycine (12%), the fibrinogen precipitate is recovered by centrifugation, and the supernatant is discarded. Said process is repeated 2 to 4 times by dissolving the precipitate in a 50 mM cystine buffer with 0.1% citrate at pH 7.0, and the precipitation is repeated with glycine. The precipitation of fibrinogen is repeated for so many times until the Factor XIII content amounts to not more than 10 mU per mL of a 1% fibrinogen solution.

As shown in Example 2, a proteolytic cleavage can largely be prevented if amino acids are used at high concentrations during the production of fibrinogen. Also as shown in Example 2, it is possible to largely eliminate harmful thrombin activities by avidous, high-molecular inhibitors. The addition of inorganic salts with chaotropic agents promotes, on the one hand, the splitting of enzyme substrate bonds, thus inhibiting the enzymatic activity and, at the same time, rendering possible a better separation of the enzymes from their substrates. For certain enzymatic effects on high-molecular substrates, the three-dimensional configuration thereof is required which is determined by a specific salt content at a certain concentration range. By complexing agents such as EDTA, said substrate configuration can be changed reversibly, whereby the effect of various enzymes on their substrates can be strongly reduced.

Virus inactivations, e.g. with detergents, have to be carried out over lengthy periods of time in the range of hours and also at room temperature or at slightly higher temperatures. Therapeutic proteins, in case they are freed insufficiently from proteases or from enzyme systems capable of forming proteases, must be mixed with sufficient amounts of protease inhibitors in order to prevent the occurrence of proteolytic damages to a therapeutic protein during virus inactivation. In Example 2, this is achieved by the addition of r-hirudin. Such may also be accomplished by the aid of antithrombin III and heparin at a ratio of 1 U of antithrombin to 6 U of heparin.

Nanofilters have proven to be particularly effective for the depletion of viruses. Nanofiltration, in particular with filters having very small pore sizes such as 20 nm and 15 nm, proceeds slowly at room temperature. By raising the temperature to up to 40° C., the speed of filtration can be substantially increased. Since the optimum temperature of most proteases lies between 35° C. and 40° C., in a sample of the solution of a therapeutic protein, which solution is to be subjected to nanofiltration, it is determined what amounts of protease inhibitors must be added in order to avoid enzymatic damage to the therapeutic protein.

For example, prothrombin complex concentrates are adjusted to a protein content of 5 mg per mL by dilution with 0.1% citrate buffer at pH 7.0 and are filtered through filters having pore sizes of 220 nm, 75 nm and 35 nm at room temperature. The filtrate of the 35 nm filtration is sterilized by filtration and filtered through filters having pore sizes of 20 nm and 15 nm (Ashia) under aseptic conditions at 40° C.±2° C. The 15 nm filtrate is ultrafiltered at refrigerator temperature. The prothrombin complex concentrate thus obtained must be pyrogen-free and must contain at least 5 U of TFPI per 100 U of prothrombin. The enzyme activity of the concentrate must not amount to more than 0.1 U of thrombin, 0.1 U of plasmin, 100 ng Factor XIa, 0.2 U of Factor Xa and 0.05 U of callicrein per 100 U, measured with chromogenic substrates.

11. Ultrasensitive Determination of Thrombin:

By an appropriate long-term incubation of an enzyme involving a suitable substrate at the optimum temperature and optimum pH thereof, a significant increase in the sensitivity of the determination of the enzyme activity can be achieved. In case of long-term incubation it is necessary to stabilize both the enzyme and the substrate. This is achieved in that the determination of the thrombin activity is carried out in a solution containing 1% polyethylene glycol having a molecular weight of between 6000 and 8000. An incubation period of 15 hours may be determined, and samples can be drawn from a thrombin stock after 3 minutes, 10 minutes, 30 minutes, 1½ hours, 5 hours and 15 hours. According to the respective substrate used, the thrombin determination may still be carried out in the range going from microunits (µU) to nanounits (nU).

In order to measure the thrombin activity during the interim storage of intermediate products or finished drug compositions, respectively, which contain therapeutic proteins sensitive to thrombin, the incubation period may also be extended to a significant extent and the temperature may be changed in accordance with the storage temperature that is required. Said process is also suitable for carrying out accelerated stability tests and for investigating the suitability of certain thrombin inhibitors. An appropriate test approach can be carried out as follows:

From a sample to be tested, a geometric dilution array comprising a 50 mM tris puffer, pH 8.3, is produced, which also contains 1% PEG (molecular weight ranging from 6000 to 8000) and NaCl at a concentration of 100 mM. Said buffer is also used for producing a 400 µM solution from the chromogenic substrate S-2238, and 500 µL of the S-2238 solution is admixed to each sample dilution. 500 µL of the S-2238 solution, to which 500 µL of tris buffer was added, is used as a control. Those stocks can be incubated at the desired temperatures (from 0° C. to 45° C.) for up to several weeks. The cleaved substrate S-2238 is measured photometrically. The absorbance value of the control is deducted from the absorbance values that were read off and the differential value is used for calculating the enzyme activity with the aid of a standard curve.

12. Determination of the Integrity of Fibrinogen by Quantifying Fibrinopeptide A:

Intact, pure fibrinogen contains less than 1 o/oo of free fibrinopeptide A. By the protease thrombin, fibrinogen is proteolytically cleaved into fibrinopeptide A and fibrinopeptide B, each having a molecular weight of about 1500, and the fibrin monomer which has a molecular weight of about 330000. At room temperature, fibrin monomers are separated from fibrinopeptides with the aid of 75% ethanol. The fibrinogen and fibrin monomer precipitated thereby is separated from the fibrinopeptides provided in the supernatant by centrifugation and the supernatant is mixed with a bentonite suspension in 75% ethanol in order to completely remove the fibrinogen and fibrin monomer. Bentonite is separated by centrifugation, the supernatant is quantitatively transferred into an evaporation flask, the bentonite sediment is suspended with 75% ethanol, is centrifugated, and the supernatant is also put into the evaporation flask. In the evaporation flask, the solution is evaporated to dryness in vacuo, and the residue is absorbed into a measured amount of buffer, and the content of fibrinopeptide A is determined by means of an Elisa test kit. The separation of fibrin and fibrin monomers by means of bentonite as described in this test kit has turned out to be insufficient (Novitec®, HiSS Diagnostics GmbH, Freiburg).

In case of a complete cleavage of fibrinogen by means of thrombin, about 5000 ng of fibrinopeptide A forms from 1000000 ng of fibrinogen. If only 1% of the present fibrinogen is cleaved, accordingly only 50 ng of fibrinopeptide A is formed. With the aid of a suitably sensitive Elisa test it is feasible to determine even 1 ng of fibrinopeptide A per mL, wherefrom the possibility arises that the fibrinogen cleavage by thrombin can be determined with sufficient accuracy throughout the entire manufacturing and storage periods of the therapeutic protein fibrinogen.

For carrying out the determination, 500 µL of the fibrinogen-containing solution to be tested, which exhibits an exactly determined fibrinogen content that has to exceed 1 mg of fibrinogen per mL, is mixed with 1500 µL of absolute alcohol, is kept at room temperature for 10 minutes, and is centrifugated for 3 minutes at between 3000 and 5000 revolutions per minute. 1 mL of the supernatant is mixed with 2 mL of an alcoholic bentonite suspension, which was obtained from 1 mL of the bentonite suspension comprising 3 mL of absolute alcohol and contained in the kit. After 10 minutes, said mixture is centrifugated following repeated, vigorous shaking. 1 mL of the supernatant is dried in a vacuum evaporator, and the dry residue is dissolved in 250 µL of tris buffer, pH 7.0. 100 µL of said solution is used for the Elisa test, and the content of fibrinopeptide A in ng is evaluated by way of a previously established standard curve. The standard curve is obtained as follows:

Fibrinopeptide A (Sigma) is dissolved using tris buffer and, by appropriate dilutions, fibrinopeptide A-solutions of 1, 2, 5, 10 and 20 ng of fibrinopeptide A per mL are obtained. 100 µL of each dilution are used in the Elisa test.

Said test is carried out as a competitive enzyme-linked Immunosorbent Assay (Elisa). 100 µL of the fibrinopeptide A-containing samples that were rid of proteins are kept in microtiter plates for one hour at room temperature together with 100 µL of an anti-fibrinopeptide A-antibody, with the wells of said microtiter plates having been pretreated with an anti-IGg-antibody. 100 µL of a fibrinopeptide A-biotin-conjugate are added to each well and incubated at room temperature for another hour. After washing the wells of the microtiter plates, 100 µL of a streptavidin-peroxydase-conjugate are added to each well, and after being left to stand at room temperature for 30 minutes, the wells of the microtiter plates are subjected to another washing. The enzyme substrate TMB is added to each well and is incubated at room temperature for 30 minutes. Thereafter, the colour development is stopped by 100 µL of 1 M hydrochloric acid, and the absorbance is measured at 450 nm. The absorbances that were read off are inversely proportional to the fibrinopeptide A-concentration of the samples whose contents of fibrinopeptide A are determined by way of a reference curve.

13. Determination of the Enzyme Inhibitor Concentration.

Determination of Antithrombin:

The principle of said determination consists in measuring an amount of inhibitors which decreases by 50% 1000 µU of thrombin in a buffer volume of 1 mL in the presence of a 200 µM concentration of the chromogenic substrate S-2238 at an incubation period of 24 hours and at 37° C.

In order to determine the amount of antithrombins, dilutions of the inhibitor in 1% PEG are added to a respective thrombin-substrate mixture and are filled up to 1 mL with tris buffer. The kinetics of the still existing thrombin activity is measured at a temperature of 37° C. at least four points in time within the 24 hours interval. The amount of inhibitors which inhibits 50% of the activity of 1000 µU of thrombin is evaluated from a previously established calibration curve. Said amount of inhibitors is arbitrarily determined as 1 antithrombin unit.

The r-hirudin purchased from Hoechst Marion Roussel which was utilized was used as a finished drug composition under the trade name Refludan and was tested for its content of arbitrary inhibitor units.

By using a tris buffer having a pH of 8.3 and the additives as indicated in Example 1, a geometric dilution array of the r-hirudin containing r-hirudin at concentrations of from 1 to 16 ng per mL is established. 500 µL of each of those hirudin solutions is mixed with 250 µL of a 800 µM solution of the chromogenic substrate S-2238 and with 250 µL of a thrombin solution comprising 4 mU of thrombin and is incubated for 24 hours at 37° C. A control only containing thrombin at a concentration of 1000 µU in a chromogenic 200 µM substrate solution S-2238 is also incubated for 24 hours at 37° C. A 24 hour incubation assay of 200 µM of S-2238 serves as a further control.

After 24 hours of incubation, the absorbance of the individual charges is measured at 405 nm and the absorbance value of the control only containing a chromogenic substrate is deducted from the absorbances that were measured. The absorbance value of the thrombin solution which only contains 1000 µU of thrombin per mL, wherefrom the blank value was deducted, is prepared as 100% of the existing thrombin activity, and the amount of hirudin which inhibits 50% of said thrombin activity is evaluated.

Various publications are cited herein, the contents of which are hereby incorporated by reference in their entireties.

6. REFERENCES

Andersson L O, Forsman N, Huang K, Larsen K, Lundin A, Pavlu B, Sandberg H, Sewerin K, Smart J. Isolation and characterization of human factor VIII: Molecular forms in commercial factor VIII concentrate, cryoprecipitate, and plasma. Proc Natl Acad Sci 1986; 83:2979-2983.

Brummel K E, Butenas S, Mann K G. An Integrated Study of Fibrinogen during Blood Coagulation. J Biol Chem 1999; 274:22862-22870.

Eaton D, Rodriguez H, Vehar G A. Proteolytic Processing of Human Factor VIII. Correlation of Specific Cleavages by Thrombin, Factor Xa, and Activated Protein C with Activation and Inactivation of Factor VIII Coagulant Activity. Biochemistry 1986; 25:505-512.

Hemker H C. Thrombin Generation in a Reconstituted System: A Comment. Thromb Haemost 2002; 87:551-552.

Johnson A J, Fulton A J. Antihemophilic Factor Stabilization. United States patents 1994 and 1996; U.S. Pat. Nos. 5,278,289 and 5,484,890.

Kunicki T J, Montgomery R R. Method for Maintaining Intact, Non-Degraded Factor VIII/Von-Willebrand Factor During Blood Processing. United States patents 1987 and 1992; U.S. Pat. Nos. 4,710,381 and 5,149,787.

Lawson J H, Kalafatis M, Stram S, Mann K G. A Model for the Tissue Factor Pathway to Thrombin. J Biol Chem 1994; 269:23357-23366.

Mann K G, Butenas S. Thrombin Generation in a Reconstituted System: A Reply. Thromb Haemost 2002; 87:552-554.

Mutch N J, Robbie L A, Booth N A. Human Thrombi Contain an Abundance of Active Thrombin. Thromb Haemost 2001; 86:1028-1034.

Rotblat F, O'Brien D P, O'Brien F J, Goodall A H, Tuddenham E G D. Purification of Human Factor VIII:C and Its Characterization by Western Blotting Using Monoclonal Antibodies. Biochemistry 1985; 24:4294-4300.

Siebenlist K R, Meh D A, Mosesson M W. Protansglutaminase (Factor XIII) Mediated Crosslinking of Fibrinogen and Fibrin. Thromb Haemost 2001; 86:1221-1228.

The invention claimed is:

1. A storable, parenteral drug composition produced from virus-safe, pharmaceutical drug substance preparations, the composition comprising (a) one or more intact therapeutic protein, wherein the therapeutic protein is selected from the group consisting of fibrinogen, Factor VIII, Factor V, Factor XIII and clotting Factors II, VII, IX and X of the prothrombin complex, and (b) an atoxic, virus-safe protease inhibitor in an amount sufficient to stabilize the therapeutic protein, wherein the protease inhibitor is $C_1$-inhibitor.

2. The storable, parenteral drug composition according to claim 1, wherein the therapeutic protein is free of enzymes that are active proteases or protease cascades, which activate zymogens of the enzymes.

3. The storable, parenteral drug composition according to claim 1, wherein the therapeutic protein is free of any cofactors or profactors which directly or indirectly promote the activities of enzymes on the therapeutic protein contained therein.

4. The storable, parenteral drug composition according to claim 1, wherein the one or more atoxic, virus-safe protease inhibitor inhibits the activation of zymogens by proteases or protease cascades as well as the proteolytic effect of the proteases formed from zymogens and acting against the therapeutic protein(s) present in the drug substance preparations.

5. The storable, parenteral drug composition according to claim 2, wherein the enzyme is an active protease.

6. The storable, parenteral drug composition according to claim 2, wherein the enzyme is a protease bound to its substrate.

7. The storable, drug composition according to claim 1, wherein the therapeutic protein is fibrinogen.

8. The storable, parenteral drug composition according to claim 1, wherein the therapeutic protein is Factor VIII.

9. The storable, parenteral drug composition according to claim 1, wherein the therapeutic protein is Factor V.

10. The storable, parenteral drug composition according to claim 1, wherein the therapeutic protein is Factor XIII.

11. The storable, parenteral drug composition according to claim 1, wherein the therapeutic protein is the clotting Factors II, VII, IX and X of the prothrombin complex.

* * * * *